US012697293B2

(12) United States Patent
Farmer et al.

(10) Patent No.: US 12,697,293 B2
(45) Date of Patent: Aug. 4, 2026

(54) NATURAL SKINCARE COMPOSITIONS

(71) Applicant: Locus Solutions IPCo, LLC, Solon, OH (US)

(72) Inventors: Sean Farmer, Ft. Lauderdale, FL (US); Ken Alibek, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 350 days.

(21) Appl. No.: 17/771,631

(22) PCT Filed: Aug. 12, 2021

(86) PCT No.: PCT/US2021/045680

§ 371 (c)(1),
(2) Date: Apr. 25, 2022

(87) PCT Pub. No.: WO2022/036051

PCT Pub. Date: Feb. 17, 2022

(65) Prior Publication Data

US 2023/0157938 A1        May 25, 2023

Related U.S. Application Data

(60) Provisional application No. 63/064,468, filed on Aug. 12, 2020.

(51) Int. Cl.
| | |
|---|---|
| *A61K 8/60* | (2006.01) |
| *A61K 8/06* | (2006.01) |
| *A61K 8/35* | (2006.01) |
| *A61K 8/36* | (2006.01) |
| *A61Q 19/04* | (2006.01) |

(52) U.S. Cl.
CPC ............... *A61K 8/604* (2013.01); *A61K 8/06* (2013.01); *A61K 8/35* (2013.01); *A61K 8/361* (2013.01); *A61Q 19/04* (2013.01)

(58) Field of Classification Search
CPC . A61K 8/14; A61K 8/64; A61K 8/361; A61K 8/553; A61K 8/604; A61Q 19/00; A61Q 19/08; A61Q 17/005
USPC ......................................................... 514/53
See application file for complete search history.

(56) References Cited

U.S. PATENT DOCUMENTS

| | | |
|---|---|---|
| 4,902,512 A | 2/1990 | Ishigami et al. |
| 5,487,899 A | 1/1996 | Davis |
| 5,756,471 A | 5/1998 | Hillion et al. |
| 5,981,497 A | 11/1999 | Maingault |
| 6,057,302 A | 5/2000 | Borzeix |
| 6,403,108 B1 | 6/2002 | Abdullah |
| 6,596,265 B1 | 7/2003 | Borzeix Concaix |
| 6,699,499 B1 | 3/2004 | Aneja |
| 6,759,057 B1 | 7/2004 | Weiner et al. |
| 9,271,908 B2 | 3/2016 | Allef et al. |
| 9,289,460 B2 | 3/2016 | Justen et al. |
| 9,499,419 B2 | 11/2016 | de Rijk |
| 9,561,255 B2 | 2/2017 | Iwama et al. |
| 9,585,903 B2 | 3/2017 | Prabhune et al. |
| 9,650,405 B2 | 5/2017 | Gross et al. |
| 9,931,309 B2 | 4/2018 | Singh et al. |
| 10,065,982 B2 | 9/2018 | Hirata et al. |
| 10,307,466 B2 | 6/2019 | Suzuki et al. |
| 2002/0123077 A1 | 9/2002 | O'Toole et al. |
| 2003/0050277 A1 | 3/2003 | Kajimoto et al. |
| 2007/0116750 A1 | 5/2007 | Wolcott |
| 2008/0311234 A1 | 12/2008 | Yoneda et al. |
| 2009/0203649 A1 | 8/2009 | Kato et al. |
| 2010/0004472 A1 | 1/2010 | Kitagawa et al. |
| 2010/0168405 A1 | 7/2010 | Suzuki et al. |
| 2010/0216197 A1 | 8/2010 | Shiraishi et al. |
| 2010/0267684 A1 | 10/2010 | Seong et al. |
| 2010/0280111 A1* | 11/2010 | Aoki .................... A61K 31/221 514/547 |
| 2011/0044972 A1 | 2/2011 | Fieldhouse et al. |
| 2011/0237531 A1 | 9/2011 | Yanagisawa et al. |
| 2012/0311741 A1 | 12/2012 | Soetaert et al. |
| 2014/0127257 A1 | 5/2014 | Schiemann et al. |
| 2014/0178444 A1 | 6/2014 | Stadler et al. |
| 2014/0296168 A1 | 10/2014 | Schilling et al. |
| 2014/0323757 A1 | 10/2014 | Kim |
| 2014/0364381 A1 | 12/2014 | Ju et al. |
| 2015/0037302 A1 | 2/2015 | Bralkowski et al. |
| 2015/0044317 A1 | 2/2015 | Farmer et al. |

(Continued)

FOREIGN PATENT DOCUMENTS

| | | |
|---|---|---|
| CN | 102465150 A | 5/2012 |
| CN | 103800224 A | 5/2014 |

(Continued)

OTHER PUBLICATIONS

Lourith et al., International Journal of Cosmetic Science, 2009, 31, 255-261.*
Arif, Clinical Cosmetic and Investigational Dermatology, 2015, 8, 455-461.*
Sacchidanand et al., Clinical Dermatology Review, 2018, 2(2), 52-63.*
Shapiro et al., Nutrition, 2001, 17, 839-844.*
Eisenstaedt, Journal of American Medical Association, 1920, 74(10), 667-671.*

(Continued)

*Primary Examiner* — Ganapathy Krishnan
(74) *Attorney, Agent, or Firm* — BENESCH, FRIEDLANDER, COPLAN & ARONOFF

(57) ABSTRACT

The topical cosmetic compositions and methods of the subject invention can be used to improve the health and/or appearance of skin by, for example, treating and/or preventing a variety of skin conditions. The invention also provides compositions and methods for enhanced sunless tanning. Biological amphiphilic molecules are used as active components, formulation enhancers and/or delivery vessels for skin active components.

2 Claims, No Drawings

(56) References Cited

U.S. PATENT DOCUMENTS

| | | | |
|---|---|---|---|
| 2015/0045290 A1 | 2/2015 | Coutte et al. | |
| 2015/0094273 A1 | 4/2015 | Prabhune et al. | |
| 2016/0030322 A1 | 2/2016 | Lu et al. | |
| 2016/0083757 A1 | 3/2016 | Fonseca et al. | |
| 2016/0101211 A1 | 4/2016 | Zimnitsky et al. | |
| 2016/0199530 A1 | 7/2016 | Ploger et al. | |
| 2016/0213757 A1 | 7/2016 | Edelson et al. | |
| 2016/0280733 A1 | 9/2016 | Araki et al. | |
| 2016/0309715 A1 | 10/2016 | Diaz de Rienzo et al. | |
| 2016/0324747 A1 | 11/2016 | Ito et al. | |
| 2016/0375071 A1 | 12/2016 | Figueroa et al. | |
| 2017/0087199 A1 | 3/2017 | Patron et al. | |
| 2017/0119638 A1 | 5/2017 | Kondo et al. | |
| 2017/0143753 A1 | 5/2017 | Gross et al. | |
| 2017/0172913 A1 | 6/2017 | Ballesteros et al. | |
| 2018/0264051 A1 | 9/2018 | Prabhune et al. | |
| 2018/0310566 A1 | 11/2018 | Sawyer et al. | |
| 2019/0231668 A1 | 8/2019 | Yoo et al. | |
| 2019/0307788 A1 | 10/2019 | Wakayama | |
| 2019/0359562 A1 | 11/2019 | Lyman et al. | |
| 2020/0155444 A1* | 5/2020 | Farmer | A61K 8/9728 |
| 2023/0405127 A1 | 12/2023 | Lefkowitz et al. | |

FOREIGN PATENT DOCUMENTS

| | | |
|---|---|---|
| CN | 104178538 A | 12/2014 |
| CN | 106890114 A | 6/2017 |
| DE | 10131796 A1 | 1/2003 |
| EP | 1212093 A0 | 6/2002 |
| EP | 1228752 A2 | 8/2002 |
| EP | 1964546 A1 | 9/2009 |
| EP | 2351847 A1 | 8/2011 |
| EP | 3117838 A1 | 1/2017 |
| GB | 2576636 A | 2/2020 |
| JP | 0710735 A | 1/1995 |
| JP | 10501260 A | 2/1998 |
| JP | 2003040767 A | 2/2003 |
| JP | 2003113040 A | 4/2003 |
| JP | 2006131589 A | 5/2006 |
| JP | 2007129973 A | 5/2007 |
| JP | 2008044855 A | 2/2008 |
| JP | 2009029788 A | 2/2009 |
| JP | 2009149566 A | 7/2009 |
| JP | 4452799 B2 | 4/2010 |
| JP | 2012051872 A | 3/2012 |
| JP | 2014034552 A | 2/2014 |
| JP | 2014058500 A | 4/2014 |
| JP | 2014114291 A | 6/2014 |
| JP | 2014150774 A | 8/2014 |
| KR | 20110012699 A | 2/2011 |
| KR | 101125189 B1 | 3/2012 |
| KR | 101608687 B1 | 4/2016 |
| RU | 2185147 C2 | 7/2002 |
| WO | 9631190 | 10/1996 |
| WO | 9850523 | 12/1998 |
| WO | 9949876 | 10/1999 |
| WO | 0054575 A2 | 9/2000 |
| WO | 2004020647 A1 | 3/2004 |
| WO | 2011008570 A2 | 1/2011 |
| WO | 2011127101 A1 | 10/2011 |
| WO | 2011134998 A1 | 11/2011 |
| WO | 2012088276 A2 | 6/2012 |
| WO | 2013003291 A2 | 1/2013 |
| WO | 2013092421 A1 | 6/2013 |
| WO | 2013112875 A1 | 8/2013 |
| WO | 2014095367 A1 | 6/2014 |
| WO | 2014120247 A1 | 8/2014 |
| WO | 2015153476 A1 | 10/2015 |
| WO | 2017044953 A1 | 3/2017 |
| WO | 2018049182 A2 | 3/2018 |
| WO | 2018129299 A1 | 7/2018 |
| WO | 2018208530 A1 | 11/2018 |
| WO | 2019051380 A1 | 3/2019 |
| WO | 2019133555 A1 | 7/2019 |
| WO | 2019227034 A1 | 11/2019 |
| WO | 2020154712 A1 | 7/2020 |
| WO | 2020185858 A1 | 9/2020 |
| WO | 2021236904 A1 | 11/2021 |
| WO | 2022174190 A1 | 8/2022 |
| WO | 2022210011 A1 | 10/2022 |

OTHER PUBLICATIONS

Ahn, C. et al. "Tuning surface-active properties of bio-surfactant sophorolipids by varying fatty-acid chain lengths." Korean Journal of Chemical Engineering 33 (2016): 2127-2133.

Bhadoriya, S.S., et al., "Biosurfactants: A New Pharmaceutical Additive for Solubility Enhancement and Pharmaceutical Development." Biochemistry & Pharmacology: Open Access, 2013, 2(2): 1-5.

Bhangale, A. P., et al. "Sophorolipids synthesized using non-traditional oils with glycerol and studies on their surfactant properties with synthetic surfactant." Tenside Surfactants Detergents 51.5 (2014): 387-396.

Bhangale, A., et al. "Production of sophorolipids synthesized on castor oil with glucose and glycerol by using Starmerella bombicola (ATCC 22214)." European Journal of Lipid Science and Technology 116.3 (2014): 336-343.

Bisht, K.S., et al. "Enzyme-mediated regioselective acylations of sophorolipids." The Journal of Organic Chemistry 64.3 (1999): 780-789.

Ciesielska, K., et al. "Exoproteome analysis of Starmerella bombicola results in the discovery of an esterase required for lactonization of sophorolipids." Journal of proteomics 98 (2014): 159-174.

De Brito, D., Biosurfactants from renewable raw materials, Universidade do Minho Departamento de Engenharia Biologica, Nov. 2013, pp. 1-93.

Delbeke, E. I. P., et al. "A new class of antimicrobial biosurfactants: quaternary ammonium sophorolipids." Green Chemistry 17.6 (2015): 3373-3377.

Delbeke, E. I. P., et al. "Chemical and enzymatic modification of sophorolipids." Green Chemistry 18.1 (2016): 76-104.

De Oliveira, M., et al., "Review: Sophorolipids A Promising Biosurfactant and it's Applications." International Journal of Advanced Biotechnology and Research, 2015, 6(2): 161-174.

Fan, L.L., et al. "Production and identification of mannosylerythritol lipid-A homologs from the ustilaginomycetous yeast Pseudozyma aphidis ZJUDM34." Carbohydrate research 392 (2014): 1-6.

Faria, N. T., et al. "Production of glycolipid biosurfactants, mannosylerythritol lipids, from pentoses and d-glucose/d- xylose mixtures by Pseudozyma yeast strains." Process Biochemistry 49.11 (2014): 1790-1799.

Imura, T., et al. "Spontaneous vesicle formation from sodium salt of acidic sophorolipid and its application as a skin penetration enhancer." Journal of oleo science 63.2 (2014): 141-147.

Ines, M., et al. "Glycolipid biosurfactants: Potential related biomedical and biotechnological applications." Carbohydrate Research 416 (2015): 59-69.

Ishii, N., et al., "Transdermal administration of lactoferrin with sophorolipid." Biochemistry and Cell Biology, 90.3 (2012): Abstract.

Joshi-Navare, K., et al., "A biosurfactant-sophorolipid acts in synergy with antibiotics to enhance their efficiency." BioMed research international, 2013.1 (2013): 1-8.

Kim, K., et al., "Characteristics of Sophorolipid as an Antimicrobial Agent." J. Microbiol. Biotechnol., 2002, 12(2): 235-241.

Kim, K., et al. "Characteristics of sophorolipid as an antimicrobial agent." Journal of microbiology and biotechnology 12.2 (2002): 235-241.

Kitamoto, D., et al., "Self-assembling properties of glycolipid biosurfactants and their potential applications." Current Opinion in Colloid & Interface Science, 14.5 (2009): 315-328.

Konishi, M., et al., "Efficient production of acid-form sophorolipids from waste glycerol and fatty acid methyl esters by Candida floricola." Journal of Oleo Science, 67.4 (2018): 489-496.

(56) References Cited

OTHER PUBLICATIONS

Kulakovskaya E., et al., "Chapter 1—Structure and Occurrence of Yeast Extracellular Glycolipids." Extracellular glycolipids of yeasts: biodiversity, biochemistry, and prospects. Academic Press, 2013, 1-13.

ScienceDirect Topics, "Critical Micelle Concentration." ScienceDirect, retrieved from Internet Oct. 24, 2023 <https://www.sciencedirect.com/topics/immunology-and-microbiology/crtical-micelle-concentration>, pp. 1-13.

Kurtzman, C. P., et al., "Production of sophorolipid biosurfactants by multiple species of the *Starmerella* (*Candida*) bombicola yeast clade." FEMS microbiology letters, 311.2 (2010): 140-146.

Lourith, N., et al., "Natural surfactants used in cosmetics: glycolipids." International journal of cosmetic science, 31.4 (2009): 255-261.

Lydon, H. L., et al., "Adjuvant antibiotic activity of acidic sophorolipids with potential for facilitating wound healing." Antimicrobial agents and chemotherapy, 61.5, e02547 (2017): 1-9.

Madankar, C. S., et al., "Review on sophorolipids—a promising microbial bio-surfactant." Tenside Surfactants Detergents, 60.2 (2023): 95-105.

Meena, K.R., et al., "Lipopeptides as the antifungal and antibacterial agents: applications in food safety and therapeutics." BioMed research international, 2015.1, 473050 (2015): 1-9.

Mintel: "GNPD—Moisturizer." Retrieved from Internet: Mar. 15, 2021, <https://www.gnpd.com/sinatra/recordpage/4643835/> pp. 1-2.

Mintel: "GNPD—Reparation U.V. Soothing After-Sun Care for Face." Retrieved from Internet: Mar. 15, 2021, <https://www.gnpd.com/sinatra/recordpage/3274251/> pp. 1-3.

Morita, T., et al., "Mannosylerythritol lipids: production and applications." Journal of Oleo Science, 64.2 (2015): 133-141.

Roelants, S.L.K.W., et al., "Towards the industrialization of new biosurfactants: biotechnological opportunities for the lactone esterase gene from Starmerella bombicola." Biotechnology and bioengineering, 113.3 (2016): 550-559.

Rowan, M.P., et al., "Burn wound healing and treatment: review and advancements." Critical care, 19 (2015): 1-12.

Saerens, K.M.J., et al., "One-step production of unacetylated sophorolipids by an acetyltransferase negative Candida bombicola." Biotechnology and bioengineering, 108.12 (2011): 2923-2931.

Santos, D.K.F., et al., "Biosurfactants: multifunctional biomolecules of the 21st century." International journal of molecular sciences, 17.3 (2016): 1-31.

Sen, R., "Biosurfactants: Advances in Experimental Medicine and Biology." Landes Bioscience and Springer Science +Business Media, LLC, 2010, 672: 1-331.

Shen, C., et al., "Targeted killing of myofibroblasts by biosurfactant di-rhamnolipid suggests a therapy against scar formation." Scientific reports, 6.1, 37553 (2016): 1-10.

Sil, J., et al., "Health care applications of different biosurfactants: Review." Int. J. Sci. Res, 6.10 (2017): 41-50.

Srivastava, R.K., et al., "Microbial originated surfactants with multiple applications: a comprehensive review." Archives of Microbiology, 204.8, 452 (2022): 1-19.

Takahashi, M., et al., "Production of sophorolipid glycolipid biosurfactants from sugarcane molasses using Starmerella bombicola NBRC 10243." Journal of Oleo Science, 60.5 (2011): 267-273.

Thaniyavarn, J., et al., "Production of sophorolipid biosurfactant by Pichia anomala." Bioscience, biotechnology, and biochemistry, 72.8 (2008): 2061-2068.

Tiwari, V.K., "Burn wound: How it differs from other wounds?" Indian journal of plastic surgery, 45.02 (2012): 364-373.

Torres Faria, N., et al., "Production of glycolipid biosurfactants, mannosylerythritol lipids, from pentoses and d-glucose/d-xylose mixtures by Pseudozyma yeast strains." Process Biochemistry, 49.11 (2014): 1790-1799.

Ueno, Y., et al., "Characterization of biosurfactant-containing liposomes and their efficiency for gene transfection." Biological and Pharmaceutical Bulletin, 30.1 (2007): 169-172.

Van Bogaert, I. N. A., et al., "Microbial production and application of sophorolipids." Applied microbiology and biotechnology, 76 (2007): 23-34.

Wadekar, S., et al., "Sophorolipid production by Starmerella bombicola (ATCC 22214) from virgin and waste frying oils, and the effects of activated earth treatment of the waste oils." Journal of the American Oil Chemists' Society, 89.6 (2012): 1029-1039.

Wang, H., et al., "Stereocontrolled syntheses of all four stereoisomeric 1, N 2-deoxyguanosine adducts of the lipid peroxidation product trans-4-hydroxynonenal." Organic Letters, 3.22 (2001): 3603-3605.

Wongsirichot, P., et al., "A review of sophorolipid production from alternative feedstocks for the development of a localized selection strategy." Journal of Cleaner Production, 319 (2021): 1-23.

Zhang, Y., et al., "Semicontinuous sophorolipid fermentation using a novel bioreactor with dual ventilation pipes and dual sieve-plates coupled with a novel separation system." Microbial biotechnology, 11.3 (2018): 455-464.

Gaby Mora: "Recipe: Walnut oil mayonnaise", Nov. 28, 2020 (Nov. 28, 2020), XP93189227, Retrieved from the Internet: mURL: https://gabymora.com.au/recipe-walnutoil-mayonnaise/: pp. 1-5.

Office Action issued in Japanese Patent Application No. 2023-509784, dated Sep. 2, 2025.

Cho, W.Y., et al., "Sophorolipids—Bio-Based Antimicrobial Formulating Agents for Applications in Food and Health", Molecules 2022, 27, 5556. https://doi.org/10.3390/molecules27175556.

* cited by examiner

NATURAL SKINCARE COMPOSITIONS

CROSS-REFERENCE TO RELATED APPLICATION

This application is a National Stage Application of International Application No. PCT/US2021/045680, filed Aug. 12, 2021; which claims priority to U.S. Provisional Patent Application No. 63/064,468, filed Aug. 12, 2020, both of which are incorporated herein by reference in their entirety.

BACKGROUND OF THE INVENTION

The skin is the largest organ of the human body. It is comprised of layers, including the epidermis, dermis, and hypodermis. The epidermis is the outermost layer and, among other things, controls water loss from cells and tissue. The dermis is the layer below the epidermis and contains blood vessels, lymph vessels, hair follicles and sweat glands. The hypodermis is mainly used for fat storage.

The outermost epidermis is made up of stratified squamous epithelium with an underlying basement membrane. It contains no blood vessels, and is nourished by diffusion from the dermis. The main types of cells that make up the epidermis are keratinocytes, with melanocytes and Langerhans cells also present. The epidermis can be further subdivided into the following strata (beginning with the outermost layer): corneum, lucidum, granulosum, spinosum, basale. Cells are formed through mitosis at the innermost layers. They move up the strata changing shape and composition as they differentiate and become filled with keratin. They eventually reach the corneum and become sloughed off. This process is called keratinization and takes place within about 30 days.

Due to the exposure of the skin, primarily the epidermis, to the environment and its purpose as a protective barrier, skin can experience long-term damage over time. Ultraviolet radiation, environmental pollution and atmospheric pollution, wind, heat, low relative humidity levels, contact with household surfactants and other chemicals, abrasives, smoking, alcohol, drugs, diet, stress, mechanical stress, severe atmospheric conditions and genetics can impact the appearance and health of the skin, with increasing exposure and/or time often resulting in increased skin damage.

Other factors, such as aging and other biochemical changes in the skin, hormonal upheavals, fatigue, stress, acne, pregnancy, tanning, diet, disease, injuries, hematomas and disorders of the blood microcirculation can also deleteriously impact the skin's appearance and/or health. Some examples of such deleterious effects on the skin include dryness, the development of fine lines and wrinkles, loss of elasticity, wasting and sagging of the skin, loss of firmness, thinning of the skin, loss of uniformity of the complexion, a dull complexion, hyperpigmentation, senile lentigines, age spots, red spots, sun spots, coarse surface texture, marbled pigmentation, scarring, and peeling.

There are several topically-applied skin care products and dermatological treatments developed to help combat these aging-related skin conditions, as well as other chronic conditions. The efficacy of these products, however, is inconsistent and often unclear. One such product is vitamin-A (retinol) and vitamin-A derivatives, called retinoids, which are topical treatments believed to work by loosening the top layer of skin and encouraging cellular turnover. Additionally, topical applications of vitamin C (ascorbic acid), which neutralizes free radicals, are used to heal skin and reduce the appearance of fine lines and wrinkles. Vitamin K is topically applied to help heal broken blood vessels, spider veins, bruises, under-eye circles and blotchy red skin. Alpha-hydroxy acids (AHAs) and beta-hydroxy acids (BHAs) are topical exfoliants that improve skin vibrancy and help prevent acne. Topical applications of epidermal growth factor (EGF) may improve skin function and create an overall more youthful appearance.

Certain chronic skin problems, such as acne, precancerous lesions, scars, pigmentation disorders, eczema, psoriasis, and seborrheic dermatitis, often require treatments such as oral medications, harsh chemical peels and topical ointments; however, many of these treatments comprise ingredients that can cause undesirable side effects, such as burning and peeling of skin, hair loss, as well as fetal harm and birth defects (if utilized while pregnant).

Another solution to maintaining a youthful appearance while protecting skin is by avoiding exposure to the sun or other sources of UV radiation. Such exposure can have deleterious effects on the skin and can, in fact, cause sunburn, skin blistering, premature skin aging or skin cancer. Self-tanning or sunless tanning compositions offer a safe alternative and enable individuals to obtain the desired suntanned appearance.

Most prominent among the sunless tanning agents is dihydroxyacetone ("DHA" which is also chemically known as 1,3-dihydroxy-2-propanone). DHA, after application, is believed to exert its effect through interactions between its hydroxyl groups and the amino groups of amino acids and peptides naturally occurring in the hydrolipid pellicle and first layers of the stratum corneum of the skin. These so-called Maillard reactions are believed to lead to formation of brown pigments in the skin, thereby giving it an appearance similar to that of a naturally obtained tan. Though the benefit of reducing exposure to harmful radiative light is achieved through the use of sunless tanning solutions, many products are difficult to apply uniformly without streaking, cause undesirable orange coloration to the skin because of improper dosing, and/or impart an unpleasant odor. These topical compositions can also contain harmful or skin-irritating synthetic additives.

Skin health is crucial for a long, healthy life. Additionally, skin health is often an external expression of beauty and youthfulness. There are a wide variety of products and treatment options for treating and/or preventing a variety of skin conditions, or otherwise enhancing the health and/or appearance of skin. Many of these treatments, however, utilize harsh prescriptions or procedures that have negative side-effects. Other, gentler options are simply not effective for everyone, or, are difficult to use effectively over-the-counter. Thus, there is a continuing need for improved, safe and effective cosmetic compositions.

BRIEF SUMMARY OF THE INVENTION

The present invention provides topical cosmetic formulations comprising multi-purpose biological amphiphilic molecules (BAMs), wherein the BAMs serve as active ingredients, formulation enhancers and/or delivery agents for active ingredients for improving the health and/or appearance of skin. Additionally, the present invention provides methods for treating and/or preventing one or more skin conditions, including chronic and/or aging-related skin conditions, using the topical composition. Advantageously, the topical compositions and methods of the present invention are environmentally-friendly, non-toxic, and cost-effective.

In certain embodiments, the topical cosmetic compositions of the present invention comprise one or more BAM having one or more direct or indirect positive effects on the appearance and/or health of skin. In some embodiments, the topical composition can further a dermatologically-acceptable carrier, and/or one or more active and/or inactive cosmetic ingredients, such as, e.g., vitamins, botanicals, dyes, fragrances, sunscreens, exfoliants, essential oils, and so on.

In some embodiments, the BAMs include biosurfactants, such as, for example, glycolipids and lipopeptides. In some embodiments, the BAMs include phospholipids and/or phospholipid mixtures. In some embodiments, the composition comprises a mixture of more than one type of BAM, such as, for example, a glycolipid and a phospholipid.

In preferred embodiments, the BAMs are produced by a living cell, for example, a microorganism. In some embodiments, the BAMs are extracted from a biological material, such as, for example, a plant or a vegetable oil. In some embodiments, the BAMs may be produced synthetically.

The BAMs of the present composition can serve one or more purposes when included in the composition. For example, the BAMs can be active ingredients, formulation enhancers and/or delivery vessels for active ingredients.

In one embodiment, the BAMs can serve as active ingredients for improving the health and/or appearance of skin by, for example, treating or preventing a skin condition such as, for example, wrinkles, sagging, dryness, roughness, peeling, eczema, psoriasis, dermatitis, age spots, hyperpigmentation, scars, keloids, stretch marks, seborrheic dermatitis, acne, body odor and others. In an exemplary embodiment, the BAMs can alter the surface of epidermis, e.g., the strata corneum or strata luceum, to improve the texture and strength, promote and/or inhibit sebum production, promote moisture retention, reduce the appearance of fine lines and wrinkles, and/or brighten the complexion. In another exemplary embodiment, the BAMs can have anti-microbial and/or anti-biofilm properties.

In one embodiment, the BAMs can serve as formulation enhancers for the topical compositions when formulated as, e.g., lotions, serums and creams. In an exemplary embodiment, the BAMs can serve as emulsifying agents (O/W and W/O), stabilizers, thickeners, emollients, preservatives, detergents, viscosity modifiers, anti-foaming agents, foaming agents, and/or UV-light guards to prevent deterioration of dyes and active ingredients. Accordingly, in some embodiments, the BAMs can be useful for improving the stability, shelf-life and appearance of cosmetic and skin care formulations.

In one embodiment, the BAMs can serve as delivery vessels and/or skin penetration enhancers, which can facilitate passage of skin active components, including other BAMs, through the epidermis and/or deliver such active components to a desired layer of the skin. In an exemplary embodiment, the BAMs can form a lipid vesicle, or liposome, with an optional active component incorporated therein. The liposome may contain a hydrophilic and/or a lipophilic active component, for example, antioxidants, vitamins, antibacterial agents, oils, anti-inflammatory agents, blood circulation promoters, lightening agents, skin conditioners, anti-aging agents, moisturizers, hormones, coloring agents, and proteins.

In certain embodiments, the composition comprises a dermatologically-acceptable carrier, such as a water-in-oil or oil-in-water emulsion, or an aqueous serum.

The topical composition can be formulated as, for example, a suspension, emulsion, nano-emulsion, hydrogel, multiphase solution, liposomal dispersion, lotion, cream, gel, foam, ointment, paste, spray, conditioner, shampoo, mask, cleanser, micellar water, tonic, makeup (e.g., lipstick, foundation, bronzer, rouge, eyeshadow), and/or after-shave.

In preferred embodiments, methods are provided for improving the health and/or appearance of skin wherein a topical cosmetic composition according to embodiments of the present invention is applied directly to an area of the subject's skin in need thereof.

In some embodiments, "applying" the composition can comprise contacting an effective amount of the composition directly with the subject's skin and, preferably, leaving the composition on the skin for a certain amount of time, e.g., about 20 seconds to 1 hour, in order for the desired aesthetic, prophylactic, therapeutic or other cosmetic benefit to be achieved. The composition can be applied using fingers or with an implement or device (e.g., a pad, cotton ball, brush, cloth, applicator pen, spray applicator, and so on).

In certain embodiments, the composition is rubbed into the skin so that the composition is absorbed therein. In some embodiments, the composition can be applied to the skin for an amount of time and then rinsed from the skin using, for example, water.

In certain embodiments, the topical cosmetic composition is applied, e.g., every other day, once daily, or twice daily. In some embodiments, the topical composition is applied every other day, once daily, or twice daily, for an indefinite period of time, e.g., for at least one, two, three weeks, or longer, in order to achieve and/or maintain the desired effect.

In some embodiments, the methods can be used to for improving a sign of aging in skin, for example, reducing the appearance of fine lines and wrinkles, reducing the appearance of age and sun spots, balancing the complexion, brightening the skin tone, smoothing the texture, and/or rejuvenating the youthful appearance of skin.

In one embodiment, the methods can be used to increase pigmentation of the skin by way of, for example, a sunless tanning composition. In other words, the compositions can be used to provide a suntanned appearance to the skin without the use of UV or other radiative light. Thus, the methods of the subject invention can be used to reduce the risk of sun burn and sun-related skin cancers by reducing a subject's desire to sunbathe.

Additionally, the methods be used to treat and/or prevent a skin condition, including, for example, acne, blemishes, rosacea, photodamage, wrinkles, sagging/looseness, dryness, age spots, scars, stretch marks, dermatitis, cellulite, keloids, lupus, psoriasis, ichtiosis, atopic dermatitis, chronic wounds, bed sores, keratosis piralis, sebaceous cysts, vitiligo, melisma, warts, inflammatory dermatoses, post inflammatory hyperpigmentation, keratoses, eczema, xerosis, pruritis, lichen planus, nodular prurigo, microbial infection, body odor, seborrheic dermatitis, burn wounds, sunburn, dandruff and miliaria.

In some embodiments, the methods can be used to remove and/or dissolve makeup, oil and other impurities on the skin.

DETAILED DESCRIPTION OF THE INVENTION

The present invention provides topical cosmetic formulations comprising multi-purpose biological amphiphilic molecules (BAM), wherein the BAM serve as active ingredients, formulation enhancers and/or delivery agents for active ingredients for improving the health and/or appearance of skin. Additionally, the present invention provides methods for treating and/or preventing one or more skin conditions, including chronic and/or aging-related skin conditions, using the topical composition. Advantageously, the topical compositions and methods of the present invention are environmentally-friendly, non-toxic, and cost-effective.

Selected Definitions

As used herein, "active ingredients," "active cosmetic ingredient" and "skin-actives" components include substances that are biologically active, meaning cause a desired therapeutic and/or cosmetic effect in the skin. This is opposed to inactive ingredients, which include excipients and/or vehicles meant for, e.g., carrying, delivering and/or stabilizing the active components, but which do not cause the desired therapeutic and/or cosmetic effect.

As used herein, the term "skin condition" encompasses any human and animal conditions, disorders, or diseases affecting the epidermis, dermis (including connective tissue, sebaceous glands and hair follicles), and/or the subcutaneous tissue (hypodermis). Skin conditions that can, in certain embodiments, be treated and/or prevented using compositions, products and methods described herein include, but are not limited to, wounds (including, e.g., burns), scars, acne, blemishes, rosacea, folliculitis, carcinoma, melanoma, general dermatitis, perioral dermatitis, cellulitis, carbuncles, photodamage, sunburn, skin aging (e.g., wrinkles and dryness), age spots, psoriasis, ichtiosis, atopic dermatitis, rashes (including but not limited to erythematosus, macular, papular and/or bullous conditions), chronic wounds, bed sores, keratosis piralis, sebaceous cysts, vitiligo, melisma, warts, inflammatory dermatoses, allodynia, ectopic dermatitis, telangiectasia, post-inflammatory hyperpigmentation, keratoses, eczema, xerosis, pruritis, lichen planus, nodular prurigo, microbial infection, body odor, scalp conditions and miliaria. Symptoms of skin conditions can include, for example, skin irritation/sensitivity, blemishes and other acneiform symptoms, pigmentation or loss thereof, flushing, inflammation, wrinkles, dryness, sagging, thickening, scaling, scarring, flaking, rash, hives, blisters, ulcers, peeling, hair loss and other changes in the health, function and appearance of the skin.

As used herein, the term "subject" refers to an animal, especially a mammal, receiving treatment, including cosmetic, over-the-counter medical care, pharmaceutical medical treatment and preventative care. The preferred subject in the context of this invention is a human. The subject can be of any age or stage of development including baby, infant, toddler, preteen, teenager, and adult. The subject can be any gender.

As used herein, "topical" means suitable for local application externally to the skin, or cutaneous application. In other words, a topical composition is not intended for application to a subject via oral, intravenous, intramuscular, intrathecal, subcutaneous, sublingual, buccal, rectal, vaginal, inhalation, ocular or otic routes.

As used herein, "dermatologically-acceptable," "cosmetically-acceptable" and "topically-acceptable" are used interchangeably and are intended to mean that a particular component is safe and non-toxic for application to the integument (e.g., skin) at the levels employed. In one embodiment, the components of the composition are recognized as being Generally Regarded as Safe (GRAS).

As used herein, the terms "effective amount," and "effective dose" are used to refer to an amount of something (e.g., a compound, a composition, time) is capable of causing a desired outcome (e.g., improvement in skin heath and/or appearance). The actual amount will vary depending on a number of factors including, but not limited to, the outcome desired, the severity of a condition being treated, the size, age, and health of the subject, and the route of administration.

As used herein, the term "treatment" refers to eradicating, reducing, ameliorating, or reversing, a degree, sign or symptom of a condition or disorder to any extent, and includes, but does not require, a complete cure of the condition or disorder. Treating can be curing, improving, or partially ameliorating a disorder.

As used herein, "preventing" a condition or disorder refers to avoiding, delaying, forestalling, or minimizing the onset of a particular sign or symptom of the condition or disorder. Prevention can, but is not required to be, absolute or complete, meaning the sign or symptom may still develop at a later time. Prevention can include reducing the severity of the onset of such a condition or disorder, and/or inhibiting the progression of the condition or disorder to a more severe condition or disorder. For example, in one embodiment, preventing hyperpigmentation can refer to avoiding, delaying, forestalling, or minimizing one or more unwanted features associated with skin hyperpigmentation, such as reducing the darkness or size of hyperpigmented areas that eventually develop. As another example, in one embodiment, preventing acne can refer to avoiding, delaying, forestalling, or minimizing one or more unwanted features associated with acne, such as reducing the number, darkness, and/or size of comedones that eventually develop, lessening the severity of acne that eventually develops, and/or completely or almost completely preventing the growth of *P. acnes*, the development of acne blemishes, and the other symptoms of acne.

As used herein, a "microbe-based composition" means a composition that comprises components that were produced as the result of the growth of microorganisms or other cell cultures. Thus, the microbe-based composition may comprise the microbes themselves and/or by-products of microbial growth (e.g., biosurfactants, solvents and/or enzymes). The cells may be in a vegetative state or in spore form, or a mixture of both. The cells may be planktonic or in a biofilm form, or a mixture of both. The cells may be intact or lysed. The cells can be present, with broth in which they were grown, at, for example, a concentration of $1\times10^4$, $1\times10^5$, $1\times10^6$, $1\times10^7$, $1\times10^8$, $1\times10^9$, $1\times10^{10}$, or $1\times10^{11}$ or more cells per milliliter of the composition. In one embodiment, the microbe-based composition may comprise only the broth in which the cells were grown, with the cells removed. The by-products of growth may be present in the broth and can include, for example, metabolites, cell membrane components, expressed proteins, and/or other cellular components.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

A "metabolite" refers to any substance produced by metabolism or a substance necessary for taking part in a particular metabolic process. A metabolite can be an organic compound that is a starting material, an intermediate in, or an end product of metabolism. Examples of metabolites can include, but are not limited to, enzymes, acids, solvents, alcohols, proteins, carbohydrates, vitamins, minerals, micro-elements, amino acids, biopolymers, and biosurfactants.

As used herein, an "isolated" or "purified" compound, e.g., a polynucleotide or polypeptide, is substantially free of other compounds, such as cellular material, genes, gene sequences, amino acids, or amino acid sequences, with which it is associated in nature and/or in which it was produced. "Isolated" in the context of a microbial strain means that the strain is removed from the environment in which it exists in nature and/or in which it is cultivated. Thus, the isolated strain may exist as, for example, a biologically pure culture, or as spores (or other forms of the strain).

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

Ranges provided herein are understood to be shorthand for all of the values within the range. For example, a range of 1 to 20 is understood to include any number, combination of numbers, or sub-range from the group consisting of 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduce" refers to a negative alteration, and "increase" refers to a positive alteration, each of at least 1%, 5%, 10%, 25%, 50%, 75%, or 100%.

As used herein, "reference" refers to a standard or control condition.

As used herein, "surfactant" refers to a compound that lowers the surface tension (or interfacial tension) between two liquids, between a liquid and a gas, or between a liquid and a solid. Surfactants act as, e.g., detergents, wetting agents, emulsifiers, foaming agents, and dispersants. A "bio-surfactant" is a surfactant produced by a living organism.

The transitional term "comprising," which is synonymous with "including," or "containing," is inclusive or open-ended and does not exclude additional, unrecited elements or method steps. By contrast, the transitional phrase "con-sisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the phrase "comprising" contemplates embodiments that "consist" and/or "consist essentially" of the recited element(s). Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example, within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Topical Cosmetic Compositions

The present invention provides skin care compositions and methods of their use. In particular, the present invention provides skin care and cosmetic products that can improve the health and/or appearance of skin by, for example, treating and/or preventing a skin condition. In certain embodiments, the composition can be used to impart a cosmetically enhancing quality to the appearance of skin.

In certain embodiments, the topical cosmetic composi-tions of the present invention comprise one or more BAM having one or more direct or indirect positive effects on the appearance and/or health of skin. In some embodiments, the topical composition can further comprise a dermatologi-cally-acceptable carrier, and one or more active or inactive cosmetic ingredients, such as, e.g., vitamins, moisturizers, dyes, fragrances, sunscreens, self-tanning pigments, exfoli-ants, essential oils, botanical extracts, and so on.

In preferred embodiments, topical cosmetic compositions are provided, comprising multi-purpose biological amphi-philic molecules (BAM), wherein the BAM serve as active ingredients, formulation enhancers and/or delivery agents for active cosmetic ingredients.

In some embodiments, the BAMs include biosurfactants, such as, for example, glycolipids and lipopeptides. In some embodiments, the BAMs include phospholipids and/or phospholipid mixtures. In some embodiments, the compo-sition comprises a mixture of more than one type of BAM, such as, for example, a glycolipid and a phospholipid.

Additional BAMs useful according to the present inven-tion include mannoprotein, beta-glucan and other metabo-lites that have bio-emulsifying and surface/interfacial ten-sion-reducing properties.

In preferred embodiments, the BAMs are produced by a living cell, for example, a microorganism. In some embodi-ments, the microbial BAMs are utilized in a crude form, wherein the molecule is present in the broth in which the microorganism is cultivated and is collected therefrom with-out purification. The crude form can comprise, for example, at least 20%, 30%, 40%, 50%, 60%, 70%, 80% or 90% w/v of the BAM in broth. In some embodiments, the BAM have been purified from the products of cultivation.

In some embodiments, the BAMs are extracted from a biological material, such as, for example, a plant or a vegetable oil. The BAM may be further purified after extraction. In some embodiments, the BAMs may be produced synthetically.

Biosurfactants

Microbially-produced surfactants, i.e., biosurfactants, are amphiphiles consisting of two parts: a polar (hydrophilic) moiety and non-polar (hydrophobic) group. Biosurfactants can include, for example, glycolipids, lipopeptides, flavolipids, phospholipids, fatty acid esters, and high-molecular-weight polymers such as lipoproteins, lipopolysaccharide-protein complexes, and/or polysaccharide-protein-fatty acid complexes.

Due to their amphiphilic structure, biosurfactants reduce the surface and interfacial tensions between the molecules of liquids, solids, and gases. Additionally, biosurfactants accumulate at interfaces, leading to the formation of aggregated micellar structures in solution. The ability of biosurfactants to form pores and destabilize biological membranes permits their use as, e.g., antibacterial and antifungal agents. Furthermore, they can inhibit microbial adhesion to a variety of surfaces, prevent the formation of biofilms, and can have powerful emulsifying and demulsifying properties.

Biosurfactants according to the subject methods can be selected from, for example, low molecular weight glycolipids (e.g., sophorolipids, cellobiose lipids, rhamnolipids, mannosylerythritol lipids and trehalose lipids), lipopeptides (e.g., surfactin, iturin, fengycin, arthrofactin and lichenysin), flavolipids, phospholipids (e.g., cardiolipins), and high molecular weight polymers such as lipoproteins, lipopolysaccharide-protein complexes, and polysaccharide-protein-fatty acid complexes.

In certain embodiments, the BAM is a glycolipid, such as mannosylerythritol lipids (MEL), sophorolipids (SLP), trehalose lipids (TL), cellobiose lipids and/or rhamnolipids (RLP). In certain embodiments, the BAM is a lipopeptide, such as a surfactin, iturin, lichenysin, arthrofactin and/or fengycin. In one embodiment, the composition can comprise a combination of any of these biosurfactants.

In one embodiment, the biosurfactants are glycolipids, which generally comprises a mono- or oligosaccharide group attached to a sphingolipid or a glycerol group that can be acetylated or alkylated, and one or more fatty acids.

In one embodiment, the glycolipid is a MEL. MEL comprise either 4-¬O—B-D-mannopyranosyl-meso-erythritol or 1-¬O—B-D-mannopyranosyl-meso-erythritol as the hydrophilic moiety, and fatty acid groups and/or acetyl groups as the hydrophobic moiety. One or two of the hydroxyls, typically at the C4 and/or C6 of the mannose residue, can be acetylated. Furthermore, there can be one to three esterified fatty acids, from 8 to 12 carbons or more in chain length.

MEL and MEL-like substances (e.g., mannose-based substances) are produced mainly by *Pseudozyma* spp. and *Ustilago* spp., with significant variability among MEL structures produced by each species. Certain mannose-based substances having similar properties to MEL can also be produced by *Meyerozyma guilliermondii* yeasts.

MEL are non-toxic and are stable at wide temperatures and pH ranges. Furthermore, MEL can be used without any additional preservatives MEL can be produced in more than 93 different combinations that fall under 5 main categories: MEL A, MEL B, MEL D, Tri-acetylated MEL A, and Tri-acetylated MEL B/C. These molecules can be modified, either synthetically or in nature. For example, MEL can comprise different carbon-length chains or different numbers of acetyl and/or fatty acid groups.

MEL molecules and/or modified forms thereof according to the subject invention can include, for example, tri-acylated, di-acylated, mono-acylated, tri-acetylated, di-acetylated, mono-acetylated and non-acetylated MEL, as well as stereoisomers and/or constitutional isomers thereof.

Other mannose-based substances/MEL-like substances that exhibit similar structures and similar properties, can also be used according to the subject invention, e.g., mannosyl-mannitol lipids (MML), mannosyl-arabitol lipids (MAL), and/or mannosyl-ribitol lipids (MRL).

Advantageously, MEL can have several benefits as active or inactive ingredients in cosmetic compositions. These can include, for example, reducing inflammation of the skin; preventing cell damage caused by the use of synthetic surfactants, such as SDS; stimulating hair bulb cells and hair growth; repairing and/or strengthening damaged hair; increasing the viability of fibroblast cells; and/or decreasing melanin content in age spots In preferred embodiments, the concentration of MEL (or MEL-like substances) in the topical cosmetic composition is from 0.001% to 90% of the total composition by weight, from 0.01% to 50%, from 0.05% to 10%, or from 0.1% to 2.0%.

In one embodiment, the glycolipid is a SLP. *Starmerella clade* yeasts, including *Candida apicola* and *Starmerella bombicola* are two major producers of SLP. SLP consist of a disaccharide sophorose linked to long chain hydroxy fatty acids. These SLPs are a partially acetylated 2-O-β-D-glucopyranosyl-D-glucopyranose unit attached β-glycosidically to 17-L-hydroxyoctadecanoic or 17-L-hydroxy-Δ9-octadecenoic acid. The hydroxy fatty acid is generally 16 or 18 carbon atoms, and may contain one or more unsaturated bonds. The fatty acid carboxyl group can be free (acidic or open form) or internally esterified at the 4"-position (lactone form).

SLP have environmental compatibility, high biodegradability, low toxicity, high selectivity and specific activity in a broad range of temperature, pH and salinity conditions.

Advantageously, SLP can have several benefits as active or inactive ingredients in cosmetic compositions. These can include, for example, emulsifying oil-in-water or water-in-oil mixtures; reducing inflammation and oxidative stress; removal of damage keratinocytes from upper layers of skin; enhancing wound healing through antimicrobial and anti-inflammatory effects; improving the metabolism of fibroblasts; improving collagen synthesis and toning/restructuring the skin; stimulating leptin synthesis through adipocytes and helping reduce subcutaneous fat overload causing cellulite; inhibiting elastase activity and reducing the appearance of wrinkles; desquamating and depigmenting spots on the skin and inhibiting melanogenisis; controlling microbial dandruff, acne and body odor; and/or reducing inflammatory conditions, such as dermatitis, eczema, and psoriasis.

In preferred embodiments, SLP concentration in the topical cosmetic composition is from 0.001% to 90% of the total composition by weight, from 0.01% to 50%, from 0.05% to 10%, or from 0.1% to 2.0%. In one embodiment, the topical composition comprises SLP in acidic form.

In a specific preferred embodiment, the topical composition of the subject invention comprises from about 0.1% to 2.0% by weight MEL, preferably about 1.0%; and further comprises from about 0.01% to about 1.0% by weight SLP, preferably about 0.5%.

In one embodiment, the glycolipid is a RLP. RLP comprise a glycosyl head group (i.e., a rhamnose) moiety, and a 3-(hydroxyalkanoyloxy)alkanoic acid (HAA) fatty acid tail, such as, e.g., 3-hydroxydecanoic acid. Two main classes of rhamnolipids exist, mono- and di-rhamnolipids, which comprise one or two rhamnose moieties, respectively. The HAA moiety can vary in length and degree of branching, depending on, for example, the growth medium and the environmental conditions.

RLPs are produced mainly by *Pseudomonas* bacteria, e.g., *P. chlororaphis*. They are natural emulsifiers, and can be used according to the subject invention to replace non-biological surfactants, such as sodium lauryl sulfate, sodium dodecyl sulfate and sodium laureth sulfate, in a cosmetic composition. Furthermore, RLPs can be formulated to increase moisture retention or to lubricate skin, minimize the appearance of wrinkles, and increase smoothness of skin. Even further, RLPs can be used as antibacterial (Gram-positive) and antifungal agents.

In preferred embodiments, RLP concentration in the topical cosmetic composition ranges from 0.001% to 90% of the total composition by weight, from 0.01% to 50%, from 0.05% to 10%, and preferably from 0.1% to 2.0%.

In one embodiment, the glycolipid is a trehalose lipid (TL). TL are glycolipids produced by, for example, the bacteria *Rhodococcus erythropolis*. TL possess emulsifying and dispersing characteristics. They exhibit increased levels of surface activity and have certain antiviral and antimicrobial properties.

In preferred embodiments, TL concentration in the topical cosmetic composition ranges from 0.001% to 90% of the total composition by weight, from 0.01% to 50%, from 0.05% to 10%, and preferably from 0.1% to 2.0%.

In some embodiments, the biosurfactant is a lipopeptide. Lipopeptides are oligopeptides synthesized by bacteria using large multi-enzyme complexes. They are frequently used as antibiotic compounds, and exhibit a wide antimicrobial spectrum of action, in addition to surfactant activities. All lipopeptides share a common cyclic structure consisting of a β-amino or β-hydroxy fatty acid integrated into a peptide moiety. Many strains of *Bacillus* spp. bacteria are capable of producing lipopeptides, for example, *Bacillus subtilis* and *Bacillus amyloliquefaciens*. In certain embodiments, the lipopeptides are produced by *B. subtilis* NRRL B-68031 and/or *B. amyloliquefaciens* NRRL B-67928.

The most commonly studied family of lipopeptides, the surfactin family, consists of heptapeptides containing a β-hydroxy fatty acid with 13 to 15 carbon atoms. Surfactins are considered some of the most powerful biosurfactants. Surfactin has high level surface activating function, and is extremely hydrophilic, forming a transparent gel at a wider range of concentrations than other biosurfactants. This biosurfactant can act as a skin penetration agent for cosmetic products, a foaming agent and an emulsifier. Furthermore, surfactin exhibits effective antibacterial (Gram-negative), antifungal and antiviral properties. Even further, surfactins may also be a key factor in the establishment of stable biofilms, while also inhibiting the biofilm formation of other bacteria, including Gram-negative bacteria.

The fengycin family, which includes plipastatins, comprises decapeptides with a β-hydroxy fatty acid. Fengycins comprise an ornithine in the peptide portion. They are capable of antifungal activity.

The iturin family, represented by, e.g., iturin A, myco-subtilin, and bacillomycin, are heptapeptides with a β-amino fatty acid. Iturins also exhibit strong antifungal activity.

In preferred embodiments, the composition comprises at a concentration of 0.001% to 90% of the total composition by weight, from 0.01% to 50%, from 0.05% to 10%, from 0.1% to 5.0%, and preferably from 0.01% to 2.0%.

Phospholipids

In certain embodiments, the BAM of the topical composition is a natural or synthetic phospholipid or a mixture of phospholipids. In preferred embodiments, the phospholipids according to the subject invention have a structure comprising a polar head consisting of at least one phosphatidic acid (PA) molecule. In some embodiments, the PA is bonded to glycerol.

Exemplary phospholipids include, but are not limited to, phosphatidic acid, lyso-phosphatidic acid, phosphatidylcholine, lysophosphatidylcholine, phosphatidylglycerol, diphosphatidylglycerol, phosphatidylglycerophosphate, phosphatidylserine, phosphatidylinositol, phosphatidylglycerophosphoglycerol, Bis(monoacylglycero)phosphate (BMP), Bis(diacylglycero)phosphate (BDP), acylphosphatidylglycerol, phosphatidylethanolamine, N-acylphosphatidylethanolamine, and cardiolipins, sphingomyelin, and plasmalogens.

In certain embodiment, lysophospholipids, hydrogenated, partially hydrogenated and/or unhydrated phospholipid derivatives, phospholipid analogs, and/or PEGylated phospholipids are utilized.

Lysophospholipids are obtained when an acyl radical is cleaved off by a phospholipase A from phospholipids (e.g. lysolecithins). Cardiolipins, such as 1,3-bisphosphatidyl glycerol, are phospholipids comprised of two phosphatidic acids linked via glycerol. Sphingomyelins are a type of sphingolipid typically comprised of a phosphorylcholine and a ceramide. Plasmalogens are ether lipids having in which the first carbon position of glycerol has an ether-linked alkene, the second carbon has a typical ester-linked fatty acid, the third carbon typically having a phospholipid head group like choline or ethanolamine.

In certain embodiments, phospholipids mixtures are utilized, which can include, but are not limited to, lecithins, including crude lecithins, lysolecithins, and lecithins that have been deoiled, fractionated, spray-dried, acetylated, hydrolyzed, hydroxylated, hydrogenated, and/or enriched with phospholipid fractions, such as phosphatidylcholine, or combinations thereof.

Lecithin is a mixture primarily composed of choline, fatty acids, glycerol, glycolipids, triglycerides, carbohydrates and phospholipids (e.g., phosphatidylcholine, phosphatidylethanolamine, phosphatidylserine and phosphatidylinositol). It can be found in egg yolks and the plasma membrane of plant and animal cells, and may be isolated either from egg yolk or from vegetable oils such as soy, safflower, canola or corn oil, from which it is extracted chemically or mechanically.

In some embodiments, the phospholipid is produced by a microorganism. In an exemplary embodiment, the microorganism is a yeast of the *Wickerhamomyces* and/or *Pichia* genera, such as, for example, *Wickerhamomyces anomalus*.

In some embodiments, the phospholipid is extracted from other natural sources, such as, for example, soybeans, safflower oil, canola oil, corn oil, egg yolk, organ meats, lean meats, cereal grains, milk, fish, roe and/or krill.

In some embodiments, the phospholipid is synthesized.

In preferred embodiments, the composition comprises at a concentration of 0.001% to 90% of the total composition by weight, from 0.01% to 50%, from 0.05% to 10%, from 0.1% to 5.0%, and preferably from 0.01% to 2.0%.

Multi-Functional BAMs

In some embodiments, the topical composition comprises a mixture of different BAMs. In one exemplary embodiment, the composition comprises a glycolipid and a phospholipid. In a specific exemplary embodiment, the composition comprises a SLP and/or a MEL with a cardiolipin and/or phosphatidylglycerol. In another specific exemplary embodiment, the composition comprises SLP and MEL, optionally with a lipopeptide or phospholipid BAM.

The BAMs can serve one or more purposes when included in the composition. For example, the BAMs can be active ingredients, formulation enhancers and/or delivery vessels for active cosmetic ingredients.

In certain embodiments, the size of a BAM and/or a micelle formed by a BAM according to the subject invention is less than 10 nm, preferably less than 8 nm, more preferably less than 5 nm. In a specific exemplary embodiment, the size of a SLP molecule and/or micelle is from 0.8 nm to 1.5 nm, or about 1.0 to 1.2 nm.

Advantageously, in certain embodiments, the small size of the subject BAMs allows for enhanced penetration thereof into nanometer-sized spaces and pores, such as, for example, the extracellular matrix of a biofilm, the cell membrane or cell wall of a microorganism, the pores of the skin, and the spaces between dermal cells and collagen fibers. Thus, the BAM of the subject invention can be more effective than larger conventional amphiphilic molecules, such as synthetic surfactants.

In one embodiment, the BAMs can serve as active ingredients for improving the health and/or appearance of skin by, for example, treating or preventing a skin condition selected from, for example, wrinkles, sagging, dryness, roughness, peeling, eczema, psoriasis, age spots, hyperpigmentation, scars, keloids, stretch marks, seborrheic dermatitis, acne, body odor and others described elsewhere herein. In an exemplary embodiment, the BAMs can alter the surface of epidermis, e.g., the strata corneum or strata luceum, to improve the texture and strength, promote and/or inhibit sebum production, promote moisture retention, reduce the appearance of fine lines and wrinkles, and/or brighten the complexion. In another exemplary embodiment, the BAMs can have anti-microbial and/or anti-biofilm properties.

In one embodiment, the BAMs can serve as formulation enhancers for the topical compositions when formulated as, e.g., lotions, serums and creams. In an exemplary embodiment, the BAMs can serve as emulsifying agents (O/W and W/O), stabilizers, thickeners, emollients, preservatives, detergent, viscosity modifiers, anti-foaming agents, foaming agents, and/or UV-light guards to prevent deterioration of dyes and active ingredients. Accordingly, in some embodiments, the BAMs can be useful for improving the stability, shelf-life and appearance of cosmetic formulations.

In one embodiment, the BAMs can serve as delivery vessels and/or skin penetration enhancers, which can facilitate passage of skin active components, including other BAMs, through the epidermis and/or deliver such active components to a desired layer of the skin. In an exemplary embodiment, the BAMs can form a lipid vesicle, or liposome, with an optional active component incorporated therein. The liposome may contain a hydrophilic and/or a lipophilic active component, for example, antioxidants, vitamins, antibacterial agents, oils, anti-inflammatory agents, blood circulation promoters, whitening agents, skin conditioners, anti-aging agents, moisturizers, hormones, coloring agents, and proteins.

Liposomes used according to the subject invention can be any of a large variety of lipid vesicles known in the art, including multilamellar vesicles, small unilamellar vesicles, large unilamellar vesicles and cochleate vesicles, and can be made according to any of a large number of production methods. Materials and procedures for forming liposomes are well-known to those skilled in the art. In general, lipids or lipophilic substances (e.g., biosurfactants and/or phospholipids) are dissolved in an organic solvent. When the solvent is removed, such as under vacuum by rotary evaporation, the lipid residue forms a film on the wall of the container.

An aqueous solution that typically contains electrolytes or hydrophilic biologically active materials is then added to the film. Sometimes, cyclodextrins or other polymers are included to enhance the stability of the liposomes. The lipid molecules line up according to polarity, with the hydrophobic tails pointing inward and the polar head groups pointing outward. In multilamellar vesicles, the polar groups at one surface of the membrane point towards the vesicle's interior and those at the other surface point toward the external environment. As a vesicle forms during its manufacture, any water-soluble molecules that have been added to the water are incorporated into the aqueous spaces in the interior of the spheres, whereas any lipid-soluble molecules added during vesicle formation are incorporated into the core of the vesicles.

Additional Components

The topical composition can be formulated as a suspension (e.g., a liposomal suspension), emulsion, nano-emulsion, hydrogel, multiphase solution, liposomal dispersion, lotion, cream, gel, essence, foam, liquid, cake, ointment, paste, serum, spray, aerosol, conditioner, shampoo, mask, cleanser, tonic, makeup (e.g., lipstick, foundation, bronzer, rouge, eyeshadow), patch, pencil, powder, towelette, soap, cleanser, stick, mousse, elixir, concentrate and/or after-shave.

The composition can be formulated within a wide range of pH levels. In one embodiment, the pH of the topical composition ranges from 1.0 to 13.0. In some embodiments, the pH of the topical composition ranges from 2.0 to 12.0. Other pH ranges suitable for the subject composition include from 3.5 to 7.0, or from 7.0 to 10.5. Suitable pH adjusters such as sodium hydroxide, citric acid and triethanolamine may be added to bring the pH within the desired range.

In certain embodiments, the topical composition comprises additional cosmetic ingredients. These components may be considered active ingredients or inactive ingredients, and can be categorized by the benefit they provide or by their postulated mode of action; however, it is to be understood that the additional components can in some instances provide more than one benefit or operate via more than one mode of action. Therefore, classifications herein are made for the sake of convenience and are not intended to limit the agent to that particular application or applications listed.

Examples of such ingredient classes include: organic solvents, silicones, pH adjusters, chelating agents, gelling agents, proteins, vitamins, emollients, oils, hydroxy acids, exfoliants, retinoids, viscosity modifiers, polymers, minerals, insect repellents, lubricants, preservatives, botanicals, clarifying agents, humectants, non-biological surfactants, antioxidants, thickeners, softeners, sunscreens, moisturizers, dyes, colorants, fragrances, abrasives, absorbents, aesthetic components such as essential oils, skin sensates, astringents, anti-acne agents, anti-caking agents, antifoaming agents, antimicrobial agents, depigmenting agents, anti-inflammatory agents, advanced glycation end-product (AGE) inhibitors, steroids, binders, biological additives, buffering agents, bulking agents, chelating agents, chemical additives, denaturants, external analgesics, keratolytic agents, desquamating agents, keratinocyte proliferation enhancers, collagenase inhibitors, elastase inhibitors, film formers or materials, opacifying agents, propellants, reducing agents, enzymes, sequestrants, skin bleaching and lightening agents, skin-conditioning agents, skin soothing and/or healing agents, thickeners, minerals, vitamins and derivatives thereof.

Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety.

The amounts of each ingredient, whether active or inactive, are those conventionally used in the cosmetic field to achieve their intended purpose, and typically range from about 0.0001% to about 25%, or from about 0.001% to about 20% of the composition, although the amounts may fall outside of these ranges. The nature of these ingredients and their amounts must be compatible with the production and function of the compositions of the disclosure.

In some embodiments, the topical composition can comprise a dermatologically acceptable or cosmetically acceptable vehicle or carrier.

The cosmetically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel, nanoemulsions or microemulsions.

As used herein, the term "oil" includes silicone oils unless otherwise indicated. The emulsion may include an emulsifier, such as a nonionic, anionic or amphoteric surfactant, or a gallant, typically in an amount from about 0.001% to about 5% by weight.

In some embodiments, the cosmetically acceptable vehicle may include water; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 1% to about 99% by weight of the composition, from 10% to about 85%, from 25% to 75%, or from 50% to about 65%.

In some embodiments, the topical cosmetic composition can comprise effective amounts of enzymes and/or proteins produced by microorganisms. For example, from about 0.001% to about 20% by weight, preferably from about 0.01% to about 15% by weight, or from about 0.05% to about 10% by weight, of one or more enzymes and/or proteins can be included. These can include, but are not limited to, exo-beta-1,3-glucanase, "killer toxins," chitinase, esterases, lipases, glycosidases, amylases, and proteases beneficial for improving skin health.

In one embodiment, the composition can comprise a botanical extract, such as, for example, caffeine, Echinacea, ginseng, glucosamine, chondroitin sulfate, garlic extract, St. John's Wort, Saw Palmetto, ginko, melatonin, beta carotene, flavonoids (e.g., anthocyanins), chia, collagen peptides, acai, activated charcoal, alfalfa, arnica, astragalus, aloe vera, ashwagandha, belladonna, berberine, bilberry, betaine, bitter melon, bitter orange, black cohosh, black psyllium, black tea, blessed thistle, blond psyllium, blueberry, blue-green algae, boron, butterbur, calendula, cannabidiol (CBD), capsaicin, capsicum, cat's claw, chamomile, chasteberry, chitosan, cinnamon, clove, coconut, cranberry, dandelion, deer velvet, devil's claw, Dong Quai, eleuthero, ephedra, eucalyptus, elderberry, evening primrose, fenugreek, feverfew, flaxseed, fucus vesiculosus, ginger, glycyrrhizin, goji, goldenseal, grape, grape seed, grapefruit, green coffee, green tea, guarana, guar gum, gymnema, hawthorn, hemp, hibiscus, honey, honokiol, hoodia, hops, horse chestnut, horny goat weed, horsetail, kava, kola nut, lavender, lemongrass, licorice root, lutein, lycopene, maca, mangosteen, methylsulfonylmethane, milk thistle, mistletoe, monolaurin, niacinamide, noni, oats, olive, oregano, palm oil, papaya, pau d'arco, peanut oil, pennyroyal, peppermint, pomegranate, propolis, quercetin, rose hip, raspberry ketone, red clover, red yeast rice, reishi mushroom, resveratrol, rose hip, sage, saw palmetto, *Satureja bachtiarica* oil, senna, slippery elm, soy, spearmint, stevia, tart cherry, tea tree oil, thunder god vine, beetroot, tellimagrandin II, turmeric, valerian, wild yam, willow bark, yerba mate, yohimbe, 5-HTP and others.

In one embodiment, the compositions comprise a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., C2-C22 alkyl esters of retinol, including retinyl palmitate, retinyl acetate, retinyl propionate). retinal, and/or retinoic acid (including all-trans retinoic acid and/or 13-cis-retinoic acid), more preferably retinoids other than retinoic acid. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate).

In one embodiment, the composition may include anti-aging components, including, but not limited to, botanicals (e.g., *Butea frondosa* extract); phytol; phytonic acid; phospholipids other than those described herein; silicones; petrolatum; triglycerides; omega fatty acids; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof). When present, the additional anti-aging compounds can be included in amounts from about 0.0001% to about 5% by weight, more typically from about 0.01% to about 2.5% by weight, or from about 0.1% to about 1.0% by weight.

In one embodiment, the composition may include an exfoliating agent. Suitable exfoliating agents include, for example, alpha-hydroxy acids, beta-hydroxy acids, oxa-acids, oxadiacids, and their derivatives, such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

In one embodiment, the composition may comprise one or more antioxidants. Suitable antioxidants include, for example, compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise, individually or collectively, from about 0.001% to about 10% (w/w), or from about 0.01% to about 5% (w/w) of the total weight of the composition.

Non-biological surfactants can also be added to the formulation. Examples of surfactants include, but are not limited to, alkyl sulfates, alkyl ether sulfates (e.g., sodium/ammonium lauryl sulfates and sodium/ammonium laureth sulfates), amphoterics (e.g., amphoacetates and amphopropionates), sulfosuccinates, alkyl polyglucosides, betaines (e.g., cocamidopropul betaine (CAPB)), sultaines, sacrosinates, isethionates, taurates, ethoxylated sorbitan esters, alkanolamides and amino-acid based surfactants.

Viscosity modifiers can also be added to the compositions, including, for example, cocamide DEA, oleamide DEA, sodium chloride, cellulosic polymers, polyacrylates, ethoxylated esters, alcohol, glycols, xylene sulfonates, polysorbate 20, alkanolamides, and cellulose derivatives (e.g., hydroxypropyl methylcellulose and hydroxyethyl cellulose).

Polymers can also be added, including, for example, xanthan gum, guar gum, polyquaternium-10, PEG-120 methyl glucose dioleate, PEG-150 distearate, PEG-150 polyglyceryl-2 tristearate and PEG-150 pentaerythrityl tetrastearate.

A sunscreen or combination of sunscreens may be included to protect the skin from both UVA and UVB rays. Among the sunscreens that can be employed in the present compositions are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1 wt % to about 30 wt % of the total weight of the composition.

In some embodiments, the composition comprises a moisturizer. The moisturizer can be provided as a humectant. In general, a humectant is a moistening agent that promotes retention of water due to its hydroscopic properties. Exemplary humectants include glycerine, polymeric glycols such as polyethylene glycol and polypropylene glycol, and sorbitols such as sorbitol solution, pyrrolidone carboxylic acid, urea, or mixtures thereof.

In some embodiments, the composition comprises an emollient for improving the texture of the composition. An emollient is an oleaginous or oily substance which helps to smooth and soften the skin, and may also reduce its roughness, cracking or irritation. Non-limiting examples of emollients include mineral oil, lanolin oil, coconut oil, cocoa butter, olive oil, almond oil, macadamia nut oil, synthetic jojoba oils, natural sonora jojoba oils, safflower oil, corn oil, liquid lanolin, cottonseed oil and peanut oil.

Other suitable emollients include squalane, castor oil, polybutene, odorless mineral spirits, sweet almond oil, avocado oil, clophyllum oil, ricin oil, vitamin E acetate, olive oil, linolenic alcohol, oleyl alcohol, the oil of cereal germs such as the oil of wheat germ, isopropyl palmitate, octyl palmitate which is commercially available as Lexol EHP, tradename of Inolex Co. of Philadelphia, Pa., isopropyl myristate, hexadecyl stearate, butyl stearate, decyl oleate, acetyl glycerides, the octanoates and benzoates of (C12-C45) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients, which are solids or semi-solids at room or ambient temperatures may be used in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myrislate, myristyl lactate, cetyl alcohol, isostearyl alcohol and isocetyl lanolate.

In some embodiments, the composition comprises a thickener to adjust the viscosity of the so that it can be readily applied to skin. Non-limiting examples of thickeners or viscosity controlling agents include cellulose gum, alkane triols; acrylates; substituted celluloses such as methylcellulose, and hydroxypropyl cellulose; hydroxyalkyl cellulose; carboxymethylcellulose; cetyl alcohol; gums such as natural gums or synthetic gums (e.g., guar gum, xanthan gum); long chain alcohols such as those having about 9 to about 24 carbon atoms; polyglycols such as polyethylene glycols, polypropylene glycols, polybutylene glycols, polyethylene propylene glycols, or mixtures thereof; waxes such as natural waxes or synthetic waxes; hydrogenated oils; glycol esters; fatty acid esters; long chain acids; acid amides; silicates; and mixtures thereof.

A coloring agent may be included in the composition to help gauge application of an even coating of the composition to skin. Exemplary coloring agents include certified dyes that are synthetic organic coal tar derivatives which are manufactured so that each batch passes a Food & Drug Administration (FDA) purity inspection. If approved by the FDA, these dyes are certified for use in foods, drugs, cosmetics (FDA colors), drugs and foods only (DC colors), or in topically applied drugs and cosmetics (External DC colors). Certified dyes can be water soluble or lakes. Lakes are organic pigments prepared by precipitating a soluble dye on a reactive or absorbent stratum which is an essential part of the pigment's composition. Most lakes are aluminum, barium or calcium derived. These insoluble pigments are used mostly in makeup products, either powders or liquids, when a temporary color is desired that will not stain the skin (as oil-soluble dyes tend to do). The lakes are used in these products along with inorganic colors such as iron oxide, zinc oxide, and titanium dioxide (the whitest white pigment).

Water-soluble dyes may also be used, e.g., FDC Blue #1, FDC Blue #2, FDC Green #3, FDC Red #3, FDC Red #40, FDC Yellow #5, FDC Yellow #6, DC Green #5, DC Red

22, DC Red #28, DC Red #33, DC Yellow #10, Ext DC Violet #2, Ext DC Yellow #7, DC Green #8, DC Orange #4, and DC Yellow #8. The water-soluble color dye can also be a natural color such as caramel color or walnut see extract color.

In some embodiments, the composition can comprise preservatives for prevention of bacterial, fungal, and/or yeast contamination. Exemplary preservatives include phenoxyethanol, benzoic acid, derivatives and salts of benzoic acid, parabens, oxazolidines, chlorinated aromatic compounds and phenols, hydantoins, cresols and derivatives, imiazolindinyl urea, iodopropanol butylcarbamate, sulfites, and bisulfites.

In some embodiments, the composition can comprise antioxidants to provide a skin benefit and/or help increase shelf life. Exemplary antioxidants that can be used include vitamins such as vitamin E, vitamin E acetate, vitamin C, vitamin A, and vitamin D, and derivatives thereof. Exemplary antioxidants include α-tocopherols which can be characterized as natural or synthetic Vitamin E. Additional exemplary antioxidants include propyl, octyl and dodecyl esters of gallic acid, butylated hydroxyanisole (BHA) (usually as a mixture of ortho and meta isomers), butylated hydroxytoluene (BHT), and nordihydroguaiaretic acid, and alkylated parabens such as methylparaben and propylparaben.

In some embodiments, the composition can comprise a chelating agent. Chelating agents are substances used to chelate or bind metallic ions with a certain heterocyclic ring structure so that the ion is held by chemical bonds from each of the participating rings. Suitable chelating agents include ethylene diaminetetraacetic acid (EDTA), EDTA trisodium, EDTA tetrasodium, calcium disodium edetate, EDTA trisodium, EDTA tetrasodium and EDTA dipotassium.

The composition may optionally comprise other components, additives or adjuvants known to those skilled in the art including, but not limited to: skin penetration enhancers; humectants (e.g., glycerin, hexylene glycol, caprylyl glycol); skin plumpers (e.g., palmitoyl oligopeptide, collagen, collagen and/or glycosaminoglycan (GAG) enhancing agents); anti-inflammatory agents (e.g., Aloe vera, bioflavonoids, diclofenac, salicylic acid); chelating agents (e.g., EDTA or a salt thereof, such as disodium EDTA); vitamins (e.g., tocopherol and ascorbic acid); vitamin derivatives (e.g., ascorbyl monopalmitate, tocopheryl acetate, Vitamin E palmitate); gelling agents (e.g., ester-terminated polyester amides); structuring agents; proteins (e.g., lactoferrin); immune modulators (e.g., corticosteroids and non-steroidal immune modulators); and tanning active components (e.g., dihydroxyacetone (DHA), 1,3,4-trihydroxy-2-butanone (Erythrulose), and botanical extracts such as *Betula alba* and *Eclipta alba*, walnut oil, jojoba, vanilla, black tea and coffee).

Methods for Improving Skin Health and/or Appearance

In preferred embodiments, methods are provided for improving the health and/or appearance of skin by, for example, treating and/or preventing a skin condition in a subject, wherein a topical cosmetic composition according to embodiments of the present invention is applied directly to an area of the subject's skin in need thereof.

In some embodiments, "applying" the composition can comprise contacting an effective amount of the composition directly with the subject's skin and, preferably, leaving the composition on the skin for a certain amount of time, e.g., about 20 seconds to 1 hour, in order for the desired aesthetic, prophylactic, therapeutic or other cosmetic benefit to be achieved. The composition can be applied using fingers or with an implement or device (e.g., a pad, cotton ball, brush, cloth, applicator pen, spray applicator, and so on).

In certain embodiments, the composition is rubbed into the skin so that the composition is absorbed therein. In some embodiments, the composition can be applied to the skin for an amount of time (e.g., in the form of a mask) and then rinsed from the skin using, for example, water.

In certain embodiments, the composition is loaded onto a patch, which can be adhered to the skin for continuous application. The patch is preferably left on the skin for a period of at least about 5 minutes, at least about 15 minutes, at least about 30 minutes or overnight while sleeping.

In one embodiment, the composition can be applied to the skin in an amount from about 0.001 to about 100 mg per $cm^2$ of skin, more typically from about 0.01 to about 20 mg/$cm^2$, or from about 0.1 to about 10 mg/$cm^2$. More or less may be used, however, depending upon the size of the area of skin to be treated.

In certain embodiments, skin of the subject's face and neck is treated according to the present methods. In some embodiments, any part of the subject's skin can be treated, including, for example, ears, chest, shoulders, back, arms, underarms, hands, stomach, buttocks, legs and feet.

In some embodiments, the methods can be used to improve the health and/or appearance of skin. In one embodiment, the present invention provides a method for improving a sign of aging, wherein a composition of the present invention is topically applied to skin in an effective amount sufficient to improve the sign of aging. Exemplary signs of aging include, but are not limited to, facial lines, fine lines, wrinkles, crow's feet, dark eye circles, blemishes, age spots, stretch marks, sagging, dryness, weakened skin barrier repair properties, or combinations thereof.

In another embodiment, the present invention provides a method for improving the aesthetic appearance of skin, in which a composition of the present invention is topically applied to skin in an effective amount sufficient to improve the aesthetic appearance of the skin. The improvements may relate to skin thickness, elasticity, resiliency, moisturization, tone, texture, radiance, luster, brightness, clarity, contour, uniformity, firmness, tautness, suppleness, softness, sensitivity, pore size, reduction in water loss, or combinations thereof.

In one embodiment, the composition provides increased pigmentation of the skin by way of, for example, a sunless tanning composition. In other words, the composition can be used to provide a suntanned appearance to the skin without the use of UV or other radiative light. Thus, the methods of the subject invention can be used to reduce the risk of sun burn and sun-related skin cancers by reducing a subject's desire to sunbathe.

Additionally, in some embodiments, the methods be used to treat and/or prevent a skin condition, affected by, resulting in or resulting from the group consisting of psoriasis, eczema, dermatitis, sunburn, estrogen imbalance, hyperpigmentation, hypopigmentation, discoloration, yellowing, freckles, skin atrophy, skin breakout, skin fragility, dryness, chapping, sagginess, thinning, hyperplasia, fibrosis, enlarged pores, cellulite formation, bruising, acne formation, acne scars, apoptosis, cellular differentiation, cellular de-differentiation, prevention of tumor induction or tumor progression, viral infections, fungal infections, bacterial infections, spider veins (telangectasia), hirsutism, rosacea, pruritis, insect bites or stings, calluses, warts, corns, photodamage, scars, keloids, lupus, ichtiosis, atopic dermatitis, chronic wounds, bed sores, keratosis piralis, sebaceous cysts, vitiligo, melisma, warts, inflammatory dermatoses, post inflammatory hyperpigmentation, keratoses, eczema, xerosis, lichen planus, nodular prurigo, microbial infection, body odor, seborrheic dermatitis, dandruff and miliaria, allergic reactions and others as described herein.

In addition to improving the aesthetic or cosmetic appearance of skin, the topical compositions of the present invention may be topically applied to enhance the general health, vitality and appearance of the skin. For example, the present composition may be applied to skin to improve microcirculation, communication among skin cells, replenishment of essential nutrients or skin constituents, or to improve the metabolism, proliferation, multiplication, turnover and/or exfoliation of skin cells.

Growth of Microbes and Production of Microbial Growth By-Products

The subject invention provides methods for cultivating microorganisms and production of microbial metabolites and/or other by-products of microbial growth. As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention provides methods of producing a microbial metabolite, including, for example, a biosurfactant, enzyme and/or other protein, by cultivating a microbe strain of the subject invention under conditions appropriate for growth and production of the metabolite. The metabolite content of the resulting culture can be, for example, at least 20%, 30%, 40%, 50%, 60%, 70%, 80%, or 90%.

The biomass content of the fermentation broth may be, for example from 5 g/l to 180 g/l or more, or 10 g/l to 150 g/l.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial culture is removed upon the completion of the cultivation (e.g., upon, for example, achieving a desired cell density, or density of a specified metabolite in the medium). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

The microorganisms can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In certain embodiments, the microbes are capable of producing amphiphilic molecules, enzymes, proteins and/or biopolymers. Microbial biosurfactants, in particular, are produced by a variety of microorganisms such as bacteria, fungi, and yeasts, including, for example, *Agrobacterium* spp. (e.g., *A. radiobacter*); *Arthrobacter* spp.; *Aspergillus* spp.; *Aureobasidium* spp. (e.g., *A. pullulans*); *Azotobacter* (e.g., *A. vinelandii, A. chroococcum*); *Azospirillum* spp. (e.g., *A. brasiliensis*); *Bacillus* spp. (e.g., *B. subtilis, B. amyloliquefaciens, B. pumillus, B. cereus, B. licheniformis, B. firmus, B. laterosporus, B. megaterium*); *Blakeslea; Candida* spp. (e.g., *C. albicans, C. rugosa, C. tropicalis, C. lipolytica, C. torulopsis*); *Clostridium* (e.g., *C. butyricum, C. tyrobutyricum, C. acetobutyricum*, and *C. beijerinckii*); *Campylobacter* spp.; *Cornybacterium* spp.; *Cryptococcus* spp.; *Debaryomyces* spp. (e.g., *D. hansenii*); *Entomophthora* spp.; *Flavobacterium* spp.; *Gordonia* spp.; *Hansenula* spp.; *Hanseniaspora* spp. (e.g., *H. uvarum*); *Issatchenkia* spp; *Kluyveromyces* spp.; *Meyerozyma* spp. (e.g., *M. guilliermondii*); *Mortierella* spp.; *Mycorrhiza* spp.; *Mycobacterium* spp.; *Nocardia* spp.; *Pichia* spp. (e.g., *P. anomala, P. guilliermondii, P. occidentalis, P. kudriavzevii*); *Phycomyces* spp.; *Phythium* spp.; *Pseudomonas* spp. (e.g., *P. aeruginosa, P. chlororaphis, P. putida, P. florescens, P. fragi, P. syringae*); *Pseudozyma* spp. (e.g., *P. aphidis*); *Ralslonia* spp. (e.g., *R. eulropha*); *Rhodococcus* spp. (e.g., *R. erythropolis*); *Rhodospirillum* spp. (e.g., *R. rubrum*); *Rhizobium* spp.;

*Rhizopus* spp.; *Saccharomyces* spp. (e.g., *S. cerevisiae, S. boulardii sequela, S. torula*); *Sphingomonas* spp. (e.g., *S. paucimobilis*); *Starmerella* spp. (e.g., *S. bombicola*); *Thraustochytrium* spp.; *Torulopsis* spp.; *Ustilago* spp. (e.g., *U. maydis*); *Wickerhamomyces* spp. (e.g., *W. anomalus*); *Williopsis* spp.; and/or *Zygosaccharomyces* spp. (e.g., *Z. bailii*).

In one embodiment, the method utilizes a yeast, such as, for example, *Wickerhamomyces anomalus, Pseudozyma aphidis, Starmerella bombicola, Pichia kudriavzevii* or *Pichia guilliermondii* (*Meyerozyma guilliermondii*). These yeasts are effective producers of various amphiphilic molecules, including phospholipids, glycolipids, enzymes and other useful metabolites.

In one embodiment, the method utilizes a bacterium, such as, for example, a *Bacillus* sp. In certain embodiments, the bacterium is *B. subtilis* B4 (strain NRRL B-68031) or *B. amyloliquefaciens* "*B. amy*" (strain NRRL B-67928).

In certain embodiments, *B. amy* is particularly advantageous due to its ability to produce a mixture of lipopeptide biosurfactants that is unique when compared with biosurfactant production capabilities of reference strains of *B. amyloliquefaciens*, as well as all *Bacillus* spp. This lipopeptide mixture comprises surfactin, lichenysin, fengycin and iturin A. In some embodiments, *B. amy* produces greater total amounts of biosurfactants compared to reference strains of *Bacillus amyloliquefaciens*.

In some embodiments, strain B4 can produce lipopeptide biosurfactants in enhanced amounts, particularly surfactin. Advantageously, in some embodiments, B4 and/or the enhanced amounts of surfactin that it produces, can be especially helpful for enhanced disruption of methanogenic biofilms in livestock digestive tracts and waste.

In some embodiments, B4 is "surfactant over-producing." For example, the strain may produce at least 0.1-10 g/L, e.g., 0.5-1 g/L biosurfactant, or, e.g., at least 10%, 25%, 50%, 100%, 2-fold, 5-fold, 7.5 fold, 10-fold, 12-fold, 15-fold or more compared to other *B. subtilis* bacteria. For example, in some embodiments, ATCC 39307 can be used as a reference strain.

Cultures of the *B. amy* and B4 strains have been deposited with the Agricultural Research Service Northern Regional Research Laboratory (NRRL) Culture Collection, 1815 N. University St. Peoria, IL, USA. The *B. amy* deposit has been assigned accession number NRRL B-67928 by the depository and was deposited on Feb. 26, 2020. The B4 deposit has been assigned accession number NRRL B-68031 by the depository and was deposited on May 6, 2021.

Each of the subject cultures has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, each of the subject culture deposits will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Other microbial strains including, for example, other strains capable of accumulating significant amounts of, for example, amphiphilic molecules, can be used in accordance with the subject invention. Additional metabolites useful according to the present invention include mannoprotein, beta-glucan and other molecules that have bio-emulsifying and surface/interfacial tension-reducing properties.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification.

However, extraction and purification can be easily achieved using standard extraction and/or purification methods or techniques described in the literature. For example, in certain embodiments, the microbe-based product comprises simply the by-products of microbial growth, either in crude or purified form. In particular embodiments, the by-products are biosurfactants produced by the microorganisms grown according to the subject invention.

The microbes and/or broth resulting from the microbial growth can be removed from the growth vessel and transferred via, for example, piping for immediate use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

In certain embodiments, the compositions of the subject invention have advantages over, for example, biosurfactants alone, including one or more of the following: high concentrations of mannoprotein as a part of yeast cell wall's outer surface (mannoprotein is a highly effective bioemulsifier capable of reaching up to an 80% emulsification index); the presence of biopolymer beta-glucan (an emulsifier) in yeast cell walls; the presence of biosurfactants in the culture, which are capable of reducing both surface and interfacial tension; and the presence of metabolites (e.g., lactic acid, ethanol, etc.).

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Example of such additives include surfactants, emulsifying agents, lubricants, buffering agents, solubility controlling agents, pH adjusting agents, preservatives, stabilizers and ultra-violet light resistant agents.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture thereof.

In one embodiment, additional components such as an aqueous preparation of a salt, such as sodium bicarbonate or carbonate, sodium sulfate, sodium phosphate, sodium biphosphate, can be included in the formulation.

Advantageously, in accordance with the subject invention, the microbe-based product may comprise the medium in which the microbes were grown. The product may be, for example, at least, by weight, 1%, 5%, 10%, 25%, 50%, 75%, or 100% growth medium. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention.

Example 1—Sunless Tanning Formulation

Sunless tanning compositions are topical compositions applied to skin to increase the pigmentation of the skin. The result is a temporary "suntan" without the use of UV or other radiative light.

In certain embodiments, the present invention provides for a topical sunless tanning formulation comprising one or more BAMs. Methods for providing a sunless tan to a subject's skin are also provided, wherein the sunless tanning composition is applied directly to the subject's skin. Preferably, the composition is applied to the skin evenly and uniformly on all parts of the skin where increased pigmentation is desired.

The methods of the subject invention can be used to reduce the risk of sun burn and sun-related skin cancers by reducing a subject's desire to sunbathe.

The sunless tanning composition of the subject invention can be formulated as, for example, an aerosol spray, a spray gel, a lotion, a foam, a cream, a mousse, a serum, a gel, a powder, and/or impregnated into a sponge, wet wipe, towelette or roller ball.

Additionally, the composition can be applied by a professional tanning salon using pressurized sunless tanning sprays. These sunless tanning sprays can be delivered over the entire body in the form of a mist, either in an enclosed booth or with a hand-held spray apparatus.

In preferred embodiments, the sunless tanning composition comprises a BAM at, for example, from 0.1% to 50% by weight, or from 0.5% to 25% by weight, or from 1.0% to 15% by weight, or from 2.0% to 10% by weight, or 3% to 5% by weight. In certain preferred embodiments, the BAM is a sophorolipid. The sophorolipid can contain a mixture of lactonic SLP, linear SLP, and/or derivatives thereof. In certain embodiments, the ratio can range from, for example, 0:1 to 1:10, or 1:4 to 1:5, linear to lactonic SLP.

Advantageously, the BAM can help maintain the composition as an emulsion, meaning it is resistant to phase separation after sitting at room temperature for a period of time include several months (e.g., from 2 to 24 months). Additionally, the BAM can maintain a sufficiently low viscosity allowing for ease of application without causing foaming. Furthermore, the BAMs can enhance application and appearance of the sunless tanning formulation by, for example, acting as a wetting agent for skin, reducing streaking, improving dispersion of active tanning components, and improving durability, sticking and penetration of coloring agents when applied to the skin.

In certain embodiments, the BAM is used in place of, or in addition to, a surfactant, including, for example, those listed elsewhere in this Description, and glycerol stearate, glycerol monostearate, polysorbate, e.g., Tween 60, polyoxyethylene stearate, and mixtures thereof.

In preferred embodiments, the composition comprises a tanning active component, so that when the composition is applied to the skin, the skin becomes darker in appearance. Non-limiting examples of tanning active components include dihydroxyacetone (DHA), 1,3,4-trihydroxy-2-butanone (Erythrulose), and botanical extracts such as *Betula alba* and *Eclipta alba*, walnut oil, jojoba, vanilla, black tea and coffee.

The tanning active component can be included in the sunless tanning composition in an amount to provide a desired level of skin darkening. In certain embodiments, the tanning active component can be included in the sunless tanning composition at about 0.1% to about 25% by weight, or about 0.5% to about 20% by weight, or about 1.0% to about 15% by weight.

In certain embodiments, the BAM helps provide a sustained release of the tanning active component so that lower levels of the active can be used to provide the desired effect. Additional, certain tanning active components can be irritating to skin at certain higher levels; thus, in some embodiments, the BAM can be useful for reducing skin irritation as a result of such applications.

In some embodiments, active tanning components can have an unpleasant odor. DHA is known for this property. Accordingly, it may be necessary to include a fragrance component and/or an odor counteractant in the sunless tanning composition. Examples of fragrances include aromatic materials extracted from botanical sources (i.e. rose petals, gardenia blossoms, jasmine flowers, etc.), which can be used alone or in any combination to create essential oils. Alternatively, alcoholic extracts may be prepared for compounding fragrances. One or more fragrances can optionally be included in the composition in an amount ranging from about 0.001 to about 10% by weight, or about 0.05 to about 5% by weight.

In addition, an odor counteractant can be used to render the sunless tanning composition relatively odorless. An exemplary odor counteractant that can be used is available under the name Ordenone from Bell Aire Fragrances. If the composition includes an odor counteractant, it can be included in an amount sufficient to counteract certain odors, e.g., about 0.05% to about 1% by weight.

In some embodiments, the sunless tanning composition can further comprise skin bonding components, maximizers, tingles, optimizers and accelerators to enhance the appearance and/or prolong the life of the sunless tanning effects.

In a specific embodiment, the composition comprises a polymeric skin bonding component, which holds the tanning active component in exposure to skin tissue for sufficient length of time to allow the tanning active component to provide a darkening effect to the skin. For example, the skin bonding component can allow the tanning component to adhere to the skin for at least 1 hour, to at least 4 hours or at least 8 hours. Advantageously, skin bonding components can reduce the time after application of the tanning composition in which a subject can shower without washing off the tanning composition.

The skin bonding component can be included in the sunless tanning composition in an amount to provide a desired level of skin darkening. In certain embodiments, the skin bonding component can be included in the sunless tanning composition at about 0.1% to about 50% by weight, or about 0.5% to about 30% by weight, or about 1.0% to about 25% by weight. In certain embodiments, the BAM of the present invention can enhance and/or replace a polymeric skin bonding component.

In some embodiments, the sunless tanning composition comprises a pH adjuster in an amount to provide a desired pH of about 3.0 to about 5.0 (e.g., an amount of about 0.1% to about 0.5% by weight). The pH adjuster can be, for example, citric acid, lactic acid, acetic acid, propionic acid, or combinations thereof.

In some embodiments, the sunless tanning composition comprises water in an amount sufficient to allow the composition to be applied to skin while providing the desired coverage of the tanning active component over the skin. The water component can be provided as, e.g., deionized water, filtered water, distilled water, reverse osmosis water, or tap water. In the event that the water includes hardness or other components, it may be desirable to include builders, sequestrants, and chelating agents to handle the water hardness. In general, the sunless tanning composition can include at least about 50% to 95% water by weight, or about 65% to about 90% water by weight.

In some embodiments, the sunless tanning composition comprises a coloring agent, such as a dye, pigment or tint. The sunless tanning composition can contain the water-soluble color dye (color indicator) in an amount sufficient to enable the composition to be readily visualized (i.e. colored) when initially applied to the skin, such that when the emulsion dries after being spread on the skin and/or is rubbed out using one's hand and/or fingers, the color substantially disappears. One or more coloring agents can be used in the composition in an amount of about 0.00001 to about 0.5% by weight of the composition, or about 0.0001 to about 0.2%, or about 0.001 to about 0.1%.

In some embodiments, the sunless tanning composition optionally comprises one or more of: a thickener at about, e.g., 0.1% to about 2.0% by weight, or about 0.5% to about 1.0% by weight; an emollient at about, e.g., 0.5% by weight to about 3% by weight, or about 1% to about 2% by weight; a moisturizer at about, e.g., 0.5% to 5.0% by weight, or about 1.0% to about 2.5% by weight; a preservatives at about, e.g., 0.25% to about 1.0% by weight, or about 0.3% to about 0.5% by weight; an antioxidant at about, e.g., 0.1% to 1.0% by weight, or about 0.2% to about 0.8% by weight; and/or a chelating agent at about, e.g., 0.001 to about 0.1% by weight.

We claim:

1. A method for improving the health and/or appearance of a subject's skin, wherein the method comprises applying, directly to the subject's skin, a topical composition consisting essentially of:

sophorolipids (SLPs);

an oat extract or salicylic acid;

one of cetyl alcohol, cetearyl alcohol, stearyl alcohol, pentylene glycol, vitamin A, and tocopherol, and a dermatologically-acceptable carrier;

wherein the sophorolipids are present in an amount from 1.0% to 15% by weight and are present in a ratio of linear to lactonic SLP of 0:1 to 1:10, and wherein the improved skin health and/or appearance is reduction in wrinkles, crow's feet, dark eye circles, blemishes, age spots, or a reduction in psoriasis, eczema, dermatitis, sunburn, rosacea, insect bites or stings, atopic dermatitis, and chronic wounds.

2. The method of claim 1, wherein the composition further comprises a mannosylerythritol lipid (MEL).

\*    \*    \*    \*    \*